United States Patent
Kataoka et al.

(10) Patent No.: US 6,861,071 B2
(45) Date of Patent: Mar. 1, 2005

(54) HIGHLY ABSORPTIVE SOLID PREPARATION

(75) Inventors: Katsuo Kataoka, Tokyo (JP); Hiroshi Kikuchi, Tokyo (JP); Tatsuya Suzuki, Tokyo (JP); Takahiro Shimaya, Tokyo (JP); Hideo Kobayashi, Tokyo (JP); Akira Kurosawa, Tokyo (JP); Koichi Ishido, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/344,044

(22) PCT Filed: Aug. 7, 2001

(86) PCT No.: PCT/JP01/06776

§ 371 (c)(1),
(2), (4) Date: Feb. 7, 2003

(87) PCT Pub. No.: WO02/11726

PCT Pub. Date: Feb. 14, 2002

(65) Prior Publication Data

US 2003/0176452 A1 Sep. 18, 2003

(30) Foreign Application Priority Data

Aug. 8, 2000 (JP) ........................................ 2000-239233

(51) Int. Cl.[7] ............................. A61K 9/20; A61K 9/48; A61F 2/00

(52) U.S. Cl. ........................ 424/464; 424/451; 424/423

(58) Field of Search ................................. 424/464, 451, 424/423, 400, 465

(56) References Cited

U.S. PATENT DOCUMENTS

| | | | | |
|---|---|---|---|---|
| 4,968,507 A | * | 11/1990 | Zentner et al. | ............. 424/465 |
| 5,587,386 A | * | 12/1996 | Hayakawa et al. | ......... 514/312 |
| 5,948,773 A | * | 9/1999 | Akiyama et al. | ........... 514/197 |
| 6,057,323 A | * | 5/2000 | Zhang et al. | .................. 514/13 |
| 6,071,962 A | * | 6/2000 | Ptchelintsev et al. | ....... 514/558 |
| 6,221,864 B1 | * | 4/2001 | Hirayama et al. | ....... 514/235.2 |

FOREIGN PATENT DOCUMENTS

| | | | |
|---|---|---|---|
| EP | 341493 | | 11/1989 |
| JP | 2-231475 | | 9/1990 |
| JP | 11-80028 | | 3/1999 |
| JP | 11-100330 | | 4/1999 |
| WO | 93/12765 | | 7/1993 |
| WO | 98/06385 | | 2/1998 |
| WO | WO 99/00136 | * | 1/1999 |
| WO | 00/015198 | | 3/2000 |

\* cited by examiner

*Primary Examiner*—James M. Spear
*Assistant Examiner*—Retford Berko
(74) *Attorney, Agent, or Firm*—Oblon, Spivak, McClelland, Maier & Neustadt, P.C.

(57) ABSTRACT

A solid preparation improved in oral absorption and reduced in fluctuations of oral absorption can be obtained by incorporating an organic acid, particularly tartaric acid, in a solid preparation having, as an active ingredient, a high content of a quinolone compound, particularly sitafloxacin, having poor water solubility at pH around neutrality.

11 Claims, No Drawings

HIGHLY ABSORPTIVE SOLID PREPARATION

TECHNICAL FIELD

The present invention relates to a solid preparation containing an active ingredient sparingly soluble in water at pH around neutrality. More specifically, the invention relates to a solid preparation having improved absorption, from the digestive tract, of an active ingredient slightly soluble in water at pH around neutrality, and to a method for improving absorption of such an active ingredient from the digestive tract.

BACKGROUND ART

Sitafloxacin [the name based on International Nonproprietary Names (INN) will hereinafter be used] is a compound (Japanese Registered Patent No. 2714597) having the following chemical structure:

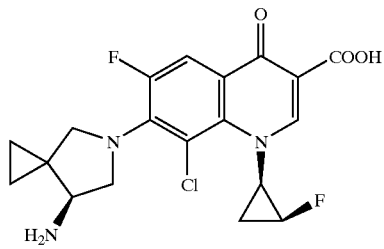

This compound has remarkably high antibacterial activities and is highly safe, so this compound under development is expected to serve as excellent quinolone synthetic antibacterials. Sitafloxacin was registered as a 3/2 hydrate under the Japanese Accepted Name (JAN). This 3/2 hydrate can be used as a sitafloxacin raw material for preparing the solid preparation of the present invention. However, it is also possible to use other types of sitafloxacin raw material, such as an anhydride, acid addition salt and carboxylate thereof.

In recent years, there has been a growing demand for the improvement of oral solid preparations, aimed to make their use more convenient to patients by reducing the number of times of dosage. In fact, improved administration methods, by which patients can reduce the number of times of dosage to as low as once per day, are prevalent in recent years. In foreign countries, particularly like European countries and the United States of America, solid preparations are generally required to contain an active ingredient at a high concentration, because people in these countries are relatively larger in their physique (body weight). For that reason, it has become necessary to obtain the solid preparations having a high concentration of an active ingredient per unit dosage. However, it turned out to have several problems such that the absorption of an active ingredient from the digestive tract is insufficient and the concentration of an active ingredient in blood varies widely, while there are no such problems with other solid preparations in which an active ingredient is contained at a small concentration. For example, sitafloxacin is known to have such tendency. More specifically, it has become apparent that some of the patients treated with the conventional solid preparations containing sitafloxacin at a high concentration are susceptible to the foregoing problems associated with the oral absorption (absorption from the digestive tract).

As a means for improving the absorption from the digestive tract, it is possible to rely on the preparations having excellent ability to disintegrate per se. In the case of sitafloxacin, however, there is no specific problem in disintegration even when incorporated in a solid preparation, and it was also confirmed that the solid preparations with excellent disintegration could be readily obtained as desired. Thus it proved that poor disintegration of a solid preparation is not responsible for a malfunction in the absorption from the digestive tract.

As another means for enhancing the absorption from the digest tract, there are the classical methods that can improve the solubility by processing an active agent, for instance, the method of pulverizing an active ingredient, the method of utilizing a solid dispersion with a high-molecular compound and the method of preparing a clatherate compound with cyclodextrin.

For the antibiotics of β-lactam type, there is a method that is capable of improving the absorption from the digestive tract by use of citric acid or cyclodextrin.

However, when used with sitafloxacin, citric acid could have a problem concerning compatibility to sitafloxacin. On the other hand, when cyclodextrin is incorporated, the composition needs to contain a large amount of this compound, to form a clatherate. The use of cyclodextrin is therefore not practical.

An object of the present invention is therefore to provide a solid preparation which contains an active ingredient at a high concentration and is free from problems in absorption from the digestive tract, more specifically, problems such as lowering of availability of the active ingredient due to poor absorption and wide variation of blood level of the active ingredient.

DISCLOSURE OF THE INVENTION

Under the foregoing circumstances, the present inventor has carried out an extensive investigation. As a result, it has been found that even absorption of a high-dose active ingredient from the digestive tract can be improved by the addition of an acid ingredient.

In the present invention, there is thus provided a solid preparation comprising (a) at least one compound selected from quinolone compounds and salts thereof, and hydrates of these quinolone compounds and salts, and (b) tartaric acid.

BEST MODE FOR CARRYING OUT THE INVENTION

The above-described quinolone compounds may be in the free form, a salt thereof or a hydrate of the free acid or the salt.

The quinolone compound, salt thereof, or hydrate of any of the foregoing is preferably a quinolone compound sparingly soluble in water at near neutral pH (about pH 7.0).

In the solid preparation of the present invention, absorption of its active ingredient from the digestive tract is improved by incorporating tartaric acid as the component of the solid preparation. This method is applicable to the production of an absorption improving preparation for a medicament, particularly of a quinolone compound, whose absorption from the digestive tract becomes poor at near neutral pH (pH 7.0) owing to sparing solubility at such a pH. The term "sparingly soluble" medicament as used herein may be interpreted as defined in the general notices of Japanese Pharmacopoeia. For example, the sparingly soluble medicament is a medicament to which a definition "sparingly soluble" or "almost insoluble" as described in the general notices can be applied. Such a medicament may be in any one of the following forms such as free form, a salt thereof, or a hydrate of any of the foregoing.

Preferred examples of the sparingly soluble quinolone compound include sitafloxacin having a chemical structure represented by the following formula:

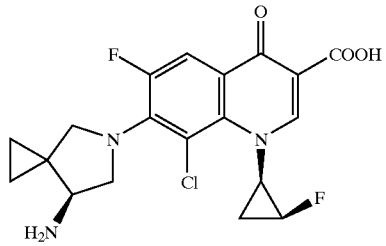

(that is, (−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid), salts thereof and hydrates of them (free form or salts).

Preferred in the present invention is a solid preparation containing, as an active ingredient, at least one of sitafloxacin, salt thereof and hydrate of sitafloxacin or its salt (a free form, salt thereof, and hydrate of sitafloxacin may hereinafter be called "sitafloxacins" collectively) and tartaric acid.

As the salt of sitafloxacin, HC1 salt, sulfuric acid salt, nitric acid salt, phosphoric acid salt, p-toluenesulfonic acid salt, methanesulfonic acid salt, fumaric acid salt and maleic acid salt can be mentioned as examples. Examples of the hydrate of sitafloxacin or its salt include 3/2 hydrate, and anhydrate is also acceptable, of which the 3/2 hydrate is usually employed.

Examples of the quinolone compound sparingly soluble in water at near neutral pH include, in addition to the above-described sitafloxacin, sparfloxacin and siprofloxacin not in the form of a hydrochloride.

The above-described solid preparation may be a tablet or a capsule, with a capsule being preferred.

The solid preparation of the present invention, which is obtained by adding an organic acid (particularly, tartaric acid) to an active ingredient having a low solubility at a neutral pH range but showing an increase in solubility at a pH higher or lower than pH 7, is improved in absorption of the active ingredient and reduced in fluctuations of its blood level.

As the tartaric acid, isomers such as d-tartaric acid, L-(+)-tartaric acid and racemic tartaric acid may be used. Of these, d-tartaric acid, especially Pharmacopoeia grade is preferred.

Existence of 0.1 time molar amount (18.3 mg) of tartaric acid together with 500 mg of sitafloxacin (as an anhydrate) brings about marked improving effects for promoting dissolution of sitafloxacin. It has been revealed that the effect becomes maximum when 0.5 time molar amount (92 mg) of tartaric acid is used in combination with 500 mg of sitafloxacin. Accordingly, tartaric acid is preferably added in an amount of 0.1 to 1 mole, preferably 1/6 mole to 0.7 mole, more preferably 0.25 to 0.5 mole, especially about 0.5 mole to 1 mole of a quinolone compound, particularly sitafloxacin.

The solid tartaric-acid-containing sitafloxacin preparation according to the present invention can be prepared using, as the other ingredients, ordinarily employed additives. Examples include excipients such as lactose, corn starch, mannitol and dibasic calcium phosphate, disintegrators such as crystalline cellulose, cros carmellose sodium, low-substitution hydroxypropyl cellulose, carboxymethyl cellulose calcium, carboxymethyl cellulose and carboxymethyl cellulose sodium, lubricants such as magnesium stearate, calcium stearate, sodium stearate, fumaric acid and hardened oil, coating agents such as macrogol and titanium oxide, binders such as hydroxypropyl cellulose, polyvinyl alcohol and hydroxypropylmethyl cellulose, and fluidizing agents such as talc. In practice, a solid preparation may be prepared in a conventional manner by using them in combination as needed.

Capsules can be prepared by the powder filling method, that is, a method of mixing an excipient, active ingredient, disintegrator, lubricant and fluidizing agent with tartaric acid and then filling capsules with the resulting mixture; or the granule filling method, that is, a method of forming granules from an excipient, base medicament (active ingredient) and binder (these granules may be coated), adding a disintegrator, lubricant, fluidizing agent and tartaric acid and filling capsules with the resulting mixture. In this case, tartaric acid may be added after granulation separately from the others and if necessary, coating. Tartaric acid mixed with the active ingredient may be granulated. Upon preparation of the granules, either dry granulation or wet granulation may be adopted.

As capsules, ordinarily employed ones can be used in this invention. For example, they may be prepared from the shell of gelatin, hydroxypropyl cellulose or starch. Of these, use of gelatin capsules is preferred.

Tablets may be formed by either one of a method of mixing an excipient, active ingredient, disintegrator, lubricant and fluidizing agent with tartaric acid and compressing the resulting mixture directly into tablets; or a method of preparing granules from an excipient, active ingredient and binder (these granules may be coated), adding tartaric acid and the other ingredients to the resulting granules and compressing the resulting mixture into tablets. In the latter case, similar to the formation of granules for capsules, tartaric acid may be granulated or tartaric acid and active ingredient are granulated together. To the thus obtained bare tablets, a coating agent may be applied. The above-described methods for preparing capsules or tablets are offered as exemplary only and the preparation process of the solid preparation of the present invention is not limited by them.

An organic acid to be incorporated is preferably tartaric acid, but an organic acid other than tartaric acid can be selected. As such an acid, any one usable as a pharmaceutical may be employed. It is needless to say that the acid does not cause any change in the composition upon preparation. Examples of such an acid include dicarboxylic acids having two carboxyl groups. Of these, dicarboxylic acids having one or plural hydroxyl groups are preferred. Examples include fumaric acid, maleic acid, malonic acid, malic acid and citric acid. Monosodium salts of such an acid may be used.

The present invention will hereinafter be described in further detail by specific examples. It should however be borne in mind that the present invention is not limited to or by them.

1) Production of Each Preparation and Injection

Sitafloxacin active ingredient (hydrate of sitafloxacin, especially 3/2 hydrate were used) and d-tartaric acid (Japanese Pharmacopoeia) were pulverized in advance (Fitzmill Pulverizer).

PREPARATION EXAMPLE 1 (COMPARATIVE EXAMPLE)

In a fluidized-bed granulator/drier (FLO-30), active ingredient (10.66 kg), sifted mannitol (11.20 kg), corn starch (4.440 kg) and low-substituted hydroxypropyl cellulose (1.500 kg) were charged. Granulation was conducted while spraying an aqueous solution (about 6 w/v %) containing hydroxypropyl cellulose (1.000 kg). After drying the resulting granules, they were shifted through a No. 16 sieve, whereby granules having a uniform size were obtained. The resulting uniform granules (28.80 kg), low-substituted hydroxypropyl cellulose (0.900 kg) and magnesium stearate (0.300 kg) were mixed in a V-shaped blender. The resulting mixture was provided as tableting granules. These tableting granules were compressed by a rotary tableting machine (HP-P15A) into caplet-type bare tablets, each about 750 mg in weight, were formed. The tablets were charged in a coating machine (Perfect Coater). Coating was applied while spraying a 10% solution of coating powder mixture "OPADRY" (Colorcon, Inc.), whereby film coated tablets, each about 767 mg in weight, were formed. In Table 1, weights of the ingredients per tablet are shown.

TABLE 1

| Ingredient | Amount per tablet (mg) |
| --- | --- |
| Sitafloxacin hydrate | 266.5 |
| (in terms of sitafloxacin) | (250) |
| D-mannitol | 280 |
| Corn starch | 111 |
| Low-substituted hydroxypropyl cellulose | 60 |
| Hydroxypropyl cellulose | 25 |
| Magnesium stearate | 7.5 |
| Total | 750 |
| OPADRY (OY-S-22845) | 17 |
| Total | 767 |

PREPARATION EXAMPLE 2 (EXAMPLE)

In a fluidized-bed granulator/drier (FLO-MINI), an active ingredient (186.5 g), sifted mannitol (33.67 g) and cross povidone (12.60 g) were charged. Granulation was conducted while spraying an aqueous solution (about 6 w/v %) containing hydroxypropyl cellulose (7.910 g). After drying the resulting granules, they were sifted through a No. 16 sieve, whereby granules having a uniform size were obtained. The resulting uniform granules (240.7 g), crystalline cellulose (33.67 g), cross povidone (53.55 g), d-tartaric acid (Japanese Pharmacopoeia; 32.20 g), magnesium stearate (3.675 g) and talc (3.675 g) were mixed, whereby tableting granules were obtained. These tableting granules were compressed by a single-punch tableting machine (KT-II) into disc-shaped tablets, each about 525 mg in weight, were formed. The tablets were charged in a coating machine (HCT-MINI) and a 10% solution of coating powder mixture "OPADRY" (Colorcon Inc.) was sprayed to them, whereby film coated tablets, each about 536 mg in weight, were formed. In Table 2, weights of ingredients per tablet are shown.

TABLE 2

| Ingredient | Amount per tablet (mg) |
| --- | --- |
| Sitafloxacin hydrate | 266.5 |
| D-mannitol | 48.1 |
| Crystalline cellulose | 48.1 |
| Cross povidone | 94.5 |
| Hydroxypropyl cellulose | 11.3 |
| d-Tartaric acid | 46.0 |

TABLE 2-continued

| Ingredient | Amount per tablet (mg) |
| --- | --- |
| (Japanese Pharmacopoeia) | |
| Magnesium stearate | 5.25 |
| Talc | 5.25 |
| Total | 525 |
| OPADRY (OY-S-22845) | 11.0 |
| Total | 536 |

PREPARATION EXAMPLE 3 (EXAMPLE)

An active ingredient (319.8 g) was charged in a fluidized-bed granulator/drier (FLO-MINI). While spraying an aqueous solution (about 2 w/v %) containing polysorbate 80 (4.320 g), they were mixed. After drying, the powder mixture was sifted through No. 30 sieve, whereby the powder mixture having a uniform particle size was obtained. The resulting uniform powder mixture (324.1 g), d-tartaric acid (Japanese Pharmacopoeia; 55.20 g), light silicic anhydride (0.360 g) and magnesium stearate (4.320 g) were mixed as a powder mixture to be filled in capsules. This powder mixture was filled in No. 0 capsules by a capsule filling machine (Dott Bonapace & Co.) so that the weight of the content in one capsule would be about 320 mg. The weights of the ingredients per tablet are shown in Table 3.

TABLE 3

| Ingredient | Weight per capsule (mg) |
| --- | --- |
| Sitafloxacin hydrate | 266.5 |
| d-Tartaric acid | 46 |
| Polysorbate 80 | 3.6 |
| Light silicic anhydride | 0.3 |
| Magnesium stearate | 3.6 |
| Total | 320 |
| White gelatin capsule No. 0 OP White | |

Production Example of Injection

An active ingredient (533.0 g) and sodium chloride (2250 g) were added to water for injection (210 L). To the resulting mixture, hydrochloric acid (concentration: 1 mol/L; 1250 mL) was added in portions, followed by the addition of water for injection (20 L) to dissolve the former in the latter at room temperature. To the resulting solution, a solution of sodium hydroxide (0.1 mol/L) was added to adjust its pH to 4.0. Water for injection was added till the concentration of sitaflexacin became a predetermined value. After membrane filtration, the resulting solution was filled in a vial, followed by high-pressure steam sterilization at 121° C. for 20 minutes.

The below-described disintegration test of the tablets (Preparation Example 1) without tartaric acid and having a high sitafloxacin content, tablets (Preparation Example 2) containing tartaric acid and having a high sitafloxacin content, and the capsules (Preparation Example 3) containing tartaric acid and having a high sitafloxacin content was conducted. These preparations were administered to human being and they were compared for bioavailability and its variation as described below.

Disintegration Test of Preparations

In accordance with the Disintegration Test Method of the General Test Method in Japanese Pharmacopoeia, the test was conducted using water as a test liquid.

Determination of the Human Plasma Level of Sitafloxacin and its Bioavailability a) Determination of the Plasma Level of Preparation Example 1

Twenty four normal volunteers (12 males and 12 females) were divided into groups at random (one group consisting of 6 volunteers). To each group member, 2 tablets of Preparation Example 1 were administered. After interval period, an injection (an amount containing 400 mg of sitafloxacin) was intravenously administered. In each case, blood was collected at proper intervals until 48 hours after administration. The blood thus collected was analyzed by liquid chromatography to determine the plasma level of sitafloxacin.

b) Calculation of the Plasma Level from Preparation Examples 2 and 3

Thirty normal volunteers (18 males and 12 females) were divided into groups at random (one group consisting of 6 volunteers). To each group member, 2 tablets of Preparation Example 2 and 2 capsules of Preparation Example 3 were administered, and an injection (400 mg in terms of sitafloxacin) was intravenously administered after a predetermined interval period. In each case, blood was collected at proper intervals until 48 hours after administration. The blood thus collected was analyzed by liquid chromatography to determine the plasma level of sitafloxacin.

c) Determination of Bioavailability

Found values not exceeding detection limit were regarded as level 0. Areas under a plasma level curve was determined by the trapezoid method from the serum levels measured for 48 hours after administration of each of the preparations. A ratio of each of the areas under the plasma level curve of Preparation Examples 1, 2 and 3 to 1.25 times the area under the plasma level curve of the injection was designated as an apparent bioavailability. At the same time, variation in apparent bioavailability among individuals were determined. Results are shown in Table 4.

TABLE 4

| Preparation/Item | Preparation Example 1: Tablet free of tartaric acid | Preparation Example 2: Tablet containing tartaric acid | Preparation Example 3: Capsule containing tartaric acid |
| --- | --- | --- | --- |
| Time spent for disintegration (min) | 3 to 5 minutes | 3 to 4 minutes | 3 to 5 minutes |
| Bioavailability | 68% | 87% | 87% |
| Variation | 38% | 23% | 19% |

As shown in Table 4, it has been revealed that there exists no difference in disintegration among preparations, but tartaric-acid-containing preparations (Preparation Examples 2 and 3) showed significant improvements in bioavailability and lowering of its fluctuations to tartaric-acid-free preparation (Preparation Example 1).

Capability of Exploitation in Industry

The present invention provides a solid preparation capable of alleviating both the malfunction and variation of the absorption of the preparation containing an active ingredient at a high concentration from the digest tract, so it is possible to reduce the number of dosage and thereby becomes more convenient to patients. In addition, the present invention provides a solid preparation containing an active ingredient at a high concentration for patients having a large physique (body weight).

What is claimed is:

1. A solid preparation consisting essentially of at least one quinolone compound and tartaric acid, wherein the at least one quinolone compound is selected from the group consisting of sitafloxacin represented by the following formula:

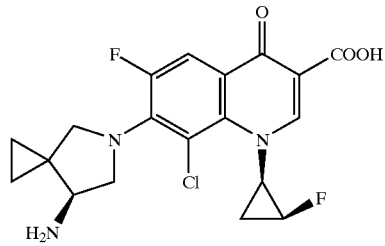

salts thereof, and hydrates thereof.

2. A solid preparation according to claim 1, which is in the form of tablets or capsules.

3. A solid preparation according to claim 2, which is in the form of capsules.

4. A solid preparation according to claim 1, comprising 0.1 to 1 mole of tartaric acid per mole of said sitafloxacin as an anhydrate.

5. A solid preparation according to claim 1, comprising 1/6 to 0.7 mole of tartaric acid per mole of said sitafloxacin as an anhydrate.

6. A solid preparation according to claim 1, comprising 0.25 to 0.5 mole of tartaric acid per mole of said sitafloxacin as an anhydrate.

7. A solid preparation according to claim 1, comprising about 0.5 mole of tartaric acid per mole of said sitafloxacin as an anhydrate.

8. A solid preparation according to claim 1, wherein the sitafloxacin as an anhydrate is present in an amount of 500 mg.

9. A solid preparation according to claim 1, which is a tablet containing the equivalent of sitafloxacin in an amount of 250 mg.

10. A solid preparation according to claim 1, which is a capsule containing the equivalent of sitafloxacin in an amount of 250 mg.

11. A solid preparation according to claim 1, which is an injectable composition containing the equivalent of sitafloxacin in an amount of 400 mg.

* * * * *